United States Patent [19]
Lawrence et al.

[11] Patent Number: 5,624,668
[45] Date of Patent: Apr. 29, 1997

[54] IRON DEXTRAN FORMULATIONS

[75] Inventors: Richard P. Lawrence, Baiting Hollow; Ralf A. Lange, Amagansett; Chin Wu, Shirley; Mary J. Helenek, Syosset, all of N.Y.

[73] Assignee: Luitpold Pharmaceuticals, Inc., Shirley, N.Y.

[21] Appl. No.: 536,984

[22] Filed: Sep. 29, 1995

[51] Int. Cl.[6] .......................... A01N 59/16; A61K 33/26
[52] U.S. Cl. .......................... 424/78.17; 424/647
[58] Field of Search .................. 424/421, 647, 424/78.17

[56] References Cited

U.S. PATENT DOCUMENTS

| Re. 24,642 | 4/1959 | London et al. |
|---|---|---|
| 2,820,740 | 1/1958 | London et al. |
| 2,885,393 | 5/1959 | Herb. |
| 3,686,397 | 8/1972 | Muller. |
| 3,697,502 | 10/1972 | Christensen. |
| 3,908,004 | 9/1975 | Kitching. |
| 4,101,435 | 7/1978 | Hasegawa et al. |
| 4,180,567 | 12/1979 | Herb. |
| 4,452,773 | 6/1984 | Molday ........................... 436/526 |
| 4,454,773 | 6/1984 | Brunner et al. |
| 4,505,726 | 3/1985 | Takeuchi et al. |
| 4,599,405 | 7/1986 | Muekker et al. |
| 4,659,697 | 4/1987 | Tanaka. |
| 4,749,695 | 6/1988 | Schwengers. |
| 4,788,281 | 11/1988 | Tosoni et al. |
| 4,927,756 | 5/1990 | Schwengers. |
| 5,102,652 | 4/1992 | Groman et al. |
| 5,118,513 | 6/1992 | Mehansho et al. |
| 5,248,492 | 9/1993 | Groman et al. |
| 5,336,506 | 8/1994 | Josephson et al. |
| 5,354,350 | 10/1994 | Moore. |

OTHER PUBLICATIONS

P. Carthew et al., *Hepatology*, vol. 13, No. 3, pp. 534–539 (1991): Rapid Induction of Hepatic Fibrosis in the Gerbil After the Parenteral Administration of Iron–Dextran Complex.

L.M. Fletcher, et al., *Gastroenterology*, vol. 97, pp. 1011–1018 (1989): Effects of Iron Loading on Free Radical Scavenging Enzymes and Lipid Peroxidation in Rat Liver.

R.D. Hamstra et al., *JAMA*, vol. 243, No. 17, pp. 1726–1731 (1980): Intravenous Iron Dextran in Clinical Medicine.

P.A. Henderson et al., *Blood*, vol. 34, No. 3, pp. 357–375 (1969): Characteristics of Iron Dextran Utilization in Man.

T. O. Pitts et al., *Nephron*, vol. 22, pp. 316–321 (1978): Hemosiderosis Secondary to Chronic Parenteral Iron Therapy in Maintenance Hemodialysis Patients.

L. R. Weintraub et al., *British Journal of Haemotology*, vol. 59, pp. 321–331 (1985): Pathogenesis of Hepatic Fibrosis in Experimental Iron Overload.

Package Insert for *INFeD* (Iron Dextran Injection, USP).
Package Insert for *Imferon* (Iron Dextran Injection, USP).
1994 ASH Abstract Reproduction Form, 36th Annual Meeting, Nashville, TN (1994): "Pharmacokinetics of Iron Dextran In Iron Deficient Dialysis Patients: Evaluation and Comparison of Two Agents", by D. Van Wyck et al.
1994 ASH Abstract Reproduction Form, 36th Annual Meeting, Nashville, TN (1994): "Iron Mobilization Early After Iron Dextran Infusion in Hemodialysis Patients: Evaluation and Comparison of 2 Agents", by D. Van Wyck et al.

*Primary Examiner*—Peter F. Kulkosky
*Attorney, Agent, or Firm*—Morrison & Foerster LLP

[57] ABSTRACT

Ferric oxyhydroxide-dextran compositions for treating iron deficiency having ellipsoidal particles with a preferred molecular weight range of about 250,000 to 300,000 daltons.

28 Claims, 6 Drawing Sheets

IRON DEXTRAN FORMULATIONS

FIELD OF THE INVENTION

The present invention relates to improved iron dextran formulations for the treatment of iron deficiency, and to methods for preparing such formulations.

BACKGROUND OF THE INVENTION

The intravenous or intramuscular injection of sterile solutions of an iron dextran complex is clinically indicated for the treatment of patients with documented iron deficiency in whom oral administration is unsatisfactory or impossible.

Iron dextran is absorbed from the injection site after intramuscular injection, for example, into the capillaries and the lymphatic system. Circulating iron dextran is cleared from the plasma by cells of the reticuloendothelial system, which split the complex into its components of iron and dextran. IMFERON®, for example, a product previously marketed by Fisons Pharmaceuticals, is released to the blood after uptake by the phagocytic activity of macrophages. See Henderson, et al., Blood 34:357–375 (1969). The iron immediately is bound to available protein moieties to form hemosiderin or ferritin, the physiological forms of iron or, to a lesser extent, to transferrin. This iron, which is subject to physiological control, replenishes the iron component of hemoglobin and other depleted iron stores.

The major benefit of the clinical use of iron dextran is that, due to its large molecular weight (i.e., greater than 70,000 daltons), the iron dextran complex is not excreted by the kidneys. Therefore almost the entire dose of iron dextran remains bioavailable as the iron dextran is metabolized in the liver. The major portion of an intramuscular injection of iron dextran is absorbed within 72 hours. Most of the remaining iron is absorbed over the ensuing 3 to 4 weeks.

Iron dextran for parenteral administration currently is marketed by Steris Pharmaceuticals, Inc. under the brand name INFeD®. As formulated, this product is a dark brown and slightly viscous sterile liquid complex of ferric oxyhydroxide, beta-FeO(OH), and is a low molecular weight dextran derivative in approximately 0.9% weight per volume sodium chloride for intravenous or intramuscular use. It contains the equivalent of 50 mg of elemental iron (as an iron dextran complex) per ml. Sodium chloride may be added for tonicity. The pH of the solution is between 5.2 and 6.5.

Under electron microscopy, IMFERON® has been shown to have an inner electron-dense FeO(OH) core with a diameter of approximately 3 nm and an outer moldable plastic dextran shell with a diameter of approximately 13 nm. Almost all of the iron, about 98–99% is present as a stable ferric-dextran complex. The remaining iron represents a very weak ferrous complex.

The dextran component of conventional iron dextran products is a polyglucose that either is metabolized or excreted. Negligible amounts of iron are lost via the urinary or alimentary pathways after administration of iron dextran. Staining from inadvertent deposition of iron dextran in subcutaneous and cutaneous tissues usually resolves or fades within several weeks or months. Various studies have reported that the half life of iron dextran in iron deficient subjects ranges from 5 to more than 20 hours. Notably, these half-life values do not represent clearance of iron from the body because iron is not readily eliminated from the body. See, for example, the package inserts for IMFERON® and INFeD®, or Hamstra, et al. JAMA 243:1726–1731 (1980).

U.S. Pat. No. 2,820,740 and its reissue RE 24,642 to London et al. describe colloidal injectable iron preparations suitable for parenteral injection formed of a nonionic ferric hydroxide, partially depolymerized dextran complex. Current commercial iron dextran products, based on these two prior patents do not have sufficient purity (see FIGS. 1 and 2) and needed thermal stability (see FIGS. 3 and 4) to safeguard safety and sterility concerns. Also, these commercial products have a relatively short plasma residence time which could cause a potential risk of iron overload in specific organs. See, Carthew, R. E., et al. Hepatology 13 (3) :534–538 (1991); Pitts, T. O., et al. Nephron 22:316 (1978); Weintraub, L. R., et al. Brit. J. Hematology 59:321 (1985); and Fletcher, L. M., et al., Gastroenterology 97:1011 (1989).

Similarly, U.S. Pat. No. 2,885,393 to Herb also discloses iron dextran complexes. The most suitable range in molecular weight of the partially depolymerized dextran for injection was found to be 30,000 to 80,000 daltons or lower. A subsequent patent to Herb, U.S. Pat. No. 4,180,567, discloses other iron preparations and methods for making and administering such preparations; however, the method disclosed does not teach the heating of iron dextran complexes above 100° C.

Other methods for the production of iron dextran complexes have been described, for example, in U.S. Pat. No. 4,599,405 to Muller et al. regarding iron (III) hydroxy/dextran complexes that are produced using an alkali carbonate, ammonium carbonate or a carbonate of an organic base added to an acid solution containing a partially depolymerized dextran and an iron (III) salt. Thereafter, an alkali metal hydroxide or ammonium hydroxide is added. The suspension so formed is then converted into a solution by heating, and the solution worked up in a known manner.

Alternatively, ferric chloride and dextran can be reacted in aqueous solution in the presence of citric acid as disclosed in U.S. Pat. No. 3,697,502 or by treating reactive trivalent iron with a complex-forming agent consisting of sorbitol, gluconic acid and certain oligosaccharides, in particular proportions and amounts as taught in U.S. Pat. No. 3,686,397.

U.S. Pat. No. 4,749,695 and its divisional, U.S. Pat. No. 4,927,756, both to Schwengers, disclose a water-soluble iron dextran and a process for its manufacture. As disclosed, the dextran utilized has an average molar mass of from 2,000 to 4,000 daltons. Another alternative includes the complexation of ferric hydroxide with hexonic acid derivatives of dextran as in U.S. Pat. No. 4,788,281 to Tosoni.

U.S. Pat. No. 3,908,004 to Kitching discloses the preparation of iron compositions to treat iron-deficiency anemia. Methods of formulating these compositions include the heating of an aqueous alkaline solution of a polysaccharide with a water soluble inorganic iron compound such as ferric oxychloride. The presence of the alkali is said to be necessary to bring about the formation of the complex. However, the alkaline conditions also cause some degradation of the polysaccharide and the low molecular-weight species so formed produce iron compounds which are responsible for undesirable effects.

U.S. Pat. No. 4,659,697 to Tanaka discloses a process for producing an organoiron (II) compound-containing antianemic composition which through the cultivation of a yeast in a saccharide-containing nutrient medium, such as grape juice, in the presence of an iron compound to form a cultured broth comprising an organoiron(II) compound, alcohol and water and removing the alcohol from the cultured broth to an extent that the resulting cultured broth has an alcohol content of less than about 1% by volume, and an antianemic composition produced thereby. The antianemic composition was said to be very stable, with excellent absorbability into a living body and incorporation of iron into hemoglobin.

Iron dextran complexes also have application as imaging agents. For example, dextran/magnetite is disclosed as a particulate solution specifically noted to be stabilized by polymeric dextran. (See Hasegawa et al., U.S. Pat. No. 4,101,435. Several others have used dextrans of various molecular weights as ingredients in the synthesis of magnetic colloids or particles. (See Hasegawa et al., U.S. Pat. No. 4,101,435; Molday, U.S. Pat. No. 4,454,773; and Schroder, U.S. Pat. No. 4,505,726. The resulting complexes of dextran and iron oxide have varying sizes and structures, but all have molecular weights of at least about 500,000 daltons.

The incorporation of high molecular weight dextran into magnetic particles or colloids may, however, cause some patients to experience adverse reactions to the dextran, particularly when such complexes are administered as parenteral magnetic resonance contrast agents. These adverse reactions may also be due in part to problems of high molecular weight polymers such as dextran dissociating from the metal oxide colloid upon prolonged storage or under high temperatures, thereby leaving the metal oxide free to aggregate.

Despite the variety of iron dextran formulations described in the prior act, current iron deficiency products are based on technology that has not satisfactorily resolved stability and purity concerns. What is needed in the therapeutic field of iron supplementation, is an improved next-generation iron dextran product with enhanced purity and thermal stability, as well as prolonged plasma residence time to minimize possible iron overload complications without compromising the efficacy of iron dextran therapy.

SUMMARY OF THE INVENTION

These and other objects are achieved by the iron dextran product prepared according to this invention. It has excellent attributes and thermal stability but also has prolonged plasma residence time to minimize possible iron overload problem without compromising the efficacy of iron dextran.

It is an object of the present invention to provide methods for synthesizing iron dextran compositions useful in the treatment of iron deficiency. Associated compositions also are disclosed. Such compositions include aqueous colloidal suspensions or solutions of a ferric oxyhydroxide-dextran complex, having an average molecular weight of about 100,000 to 600,000 daltons and a substantially uniform size distribution. Physiologically acceptable carriers for these compositions also are contemplated. The administration of such compositions to humans and other mammals for the treatment of iron deficiency or, in the case of non-human mammals, for medicinal as well as investigational purposes also are described.

In a preferred embodiment of the present invention, the molecular weight range of the iron dextran compositions are about 150,000 to 350,000 daltons, and more particularly preferred are compositions with a molecular weight range of about 250,000 to 300,000 daltons.

It is a further object of the present invention to provide iron dextran compositions having a beta-FeO(OH) core. A further object of the invention is to provide ellipsoidal iron-dextran particles with a length in the range of about 25 to 45 nanometers, more preferably about 31.5 to 36.5 nanometers, and a width of about 3.5 to 5.5 nanometers, more preferably about 4 to 5 nanometers.

It is a further object of the present invention to provide methods for synthesizing iron-dextran compositions as described above. The process of the present invention involves the initial production of iron-dextran particles by conventional methods. Applicants, however, have discovered that superior particles may be produced by the following process. Generally, as discussed in greater detail below, iron-dextran particles are purified by conventional techniques to remove various impurities, in particular, chloride iron, but also including any toxic by-products, uncomplexed dextran and, generally, any component of the initial iron-dextran reaction mixture which would not be appropriate or permitted to be administered to patients in an approvable composition.

BRIEF DESCRIPTION OF THE DRAWING FIGURES

DESCRIPTION OF THE PREFERRED EMBODIMENTS

Figure 1:
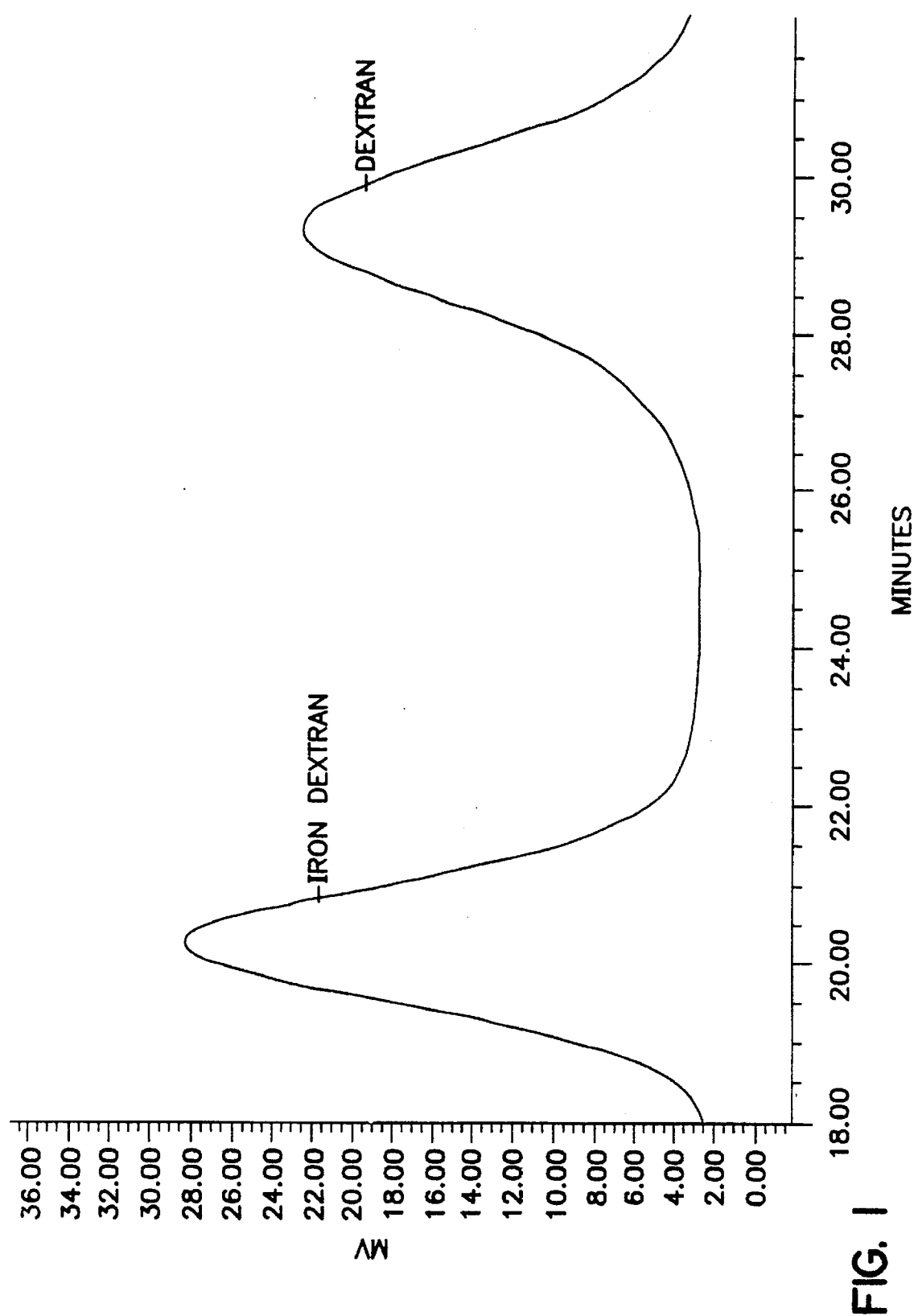
FIG. 1 shows a HPGPC chromatogram of an iron dextran formulation according to the present invention demonstrating its uniform molecular weight distribution.
Figure 2:
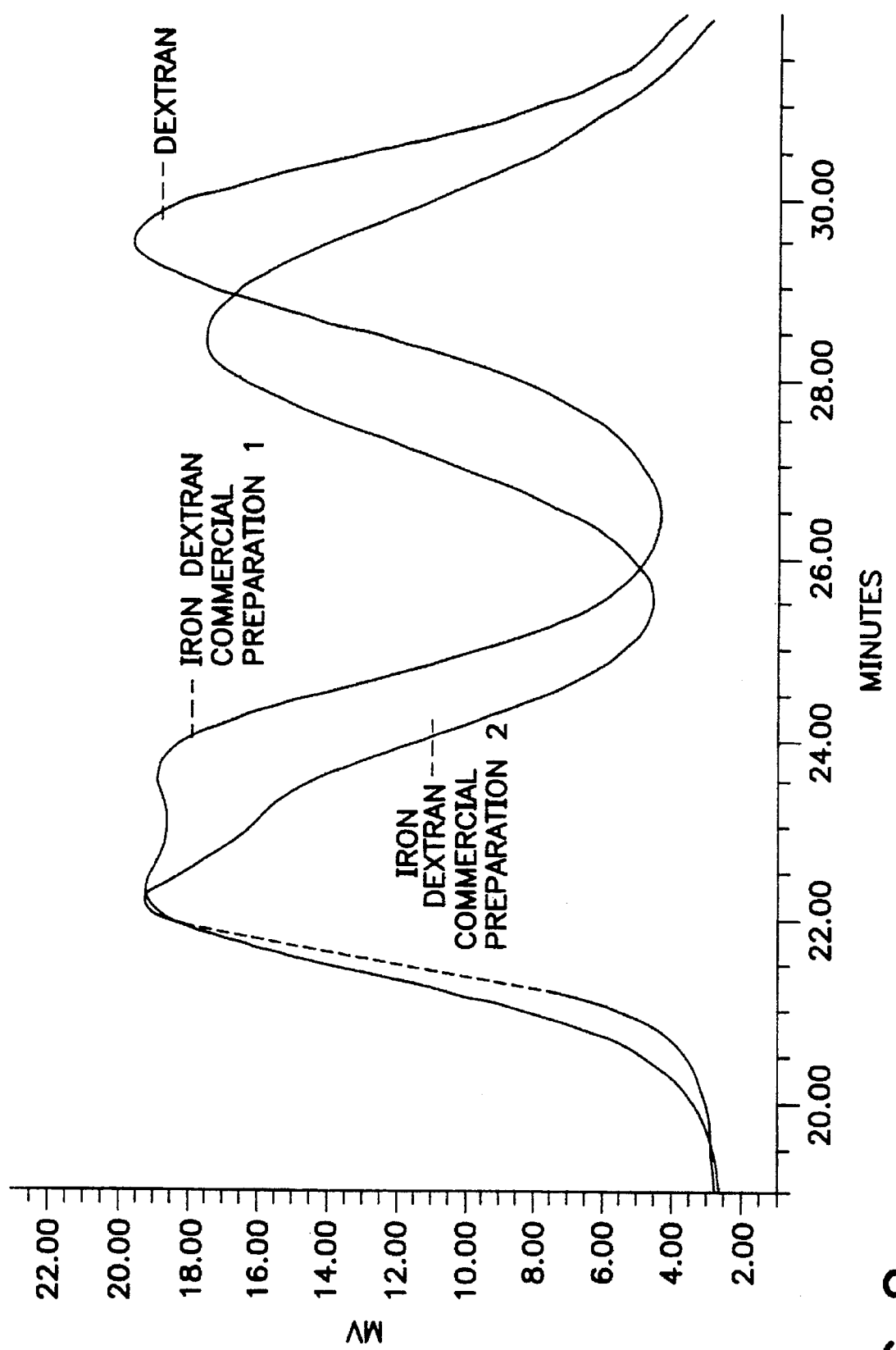
FIG. 2 shows the HPGPC chromatogram of two commercial preparations of iron dextran demonstrating a significant heterogeneity relative to the formulations in FIG. 1.
Figure 3:
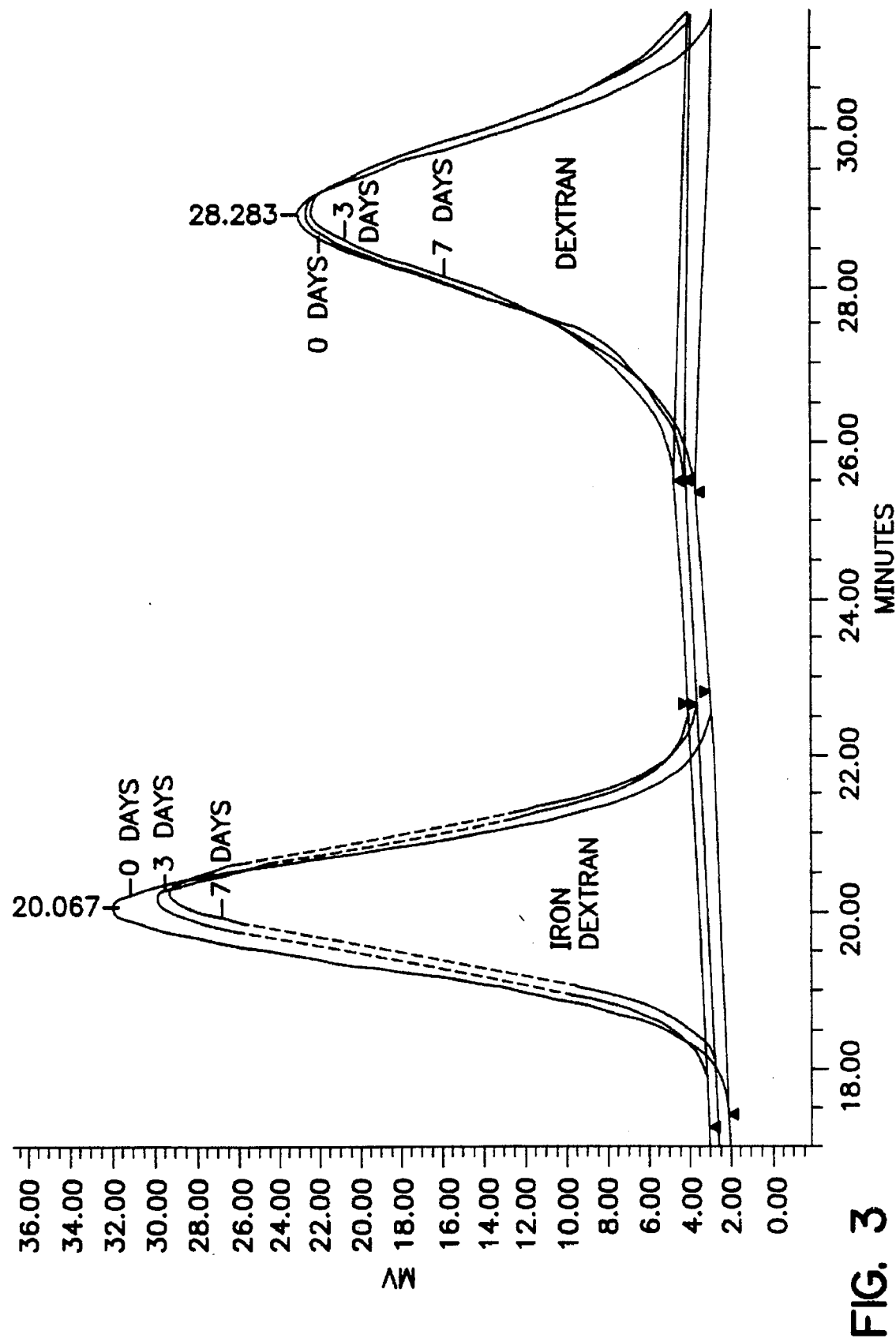
FIG. 3 shows the HPGPC chromatogram of an iron dextran formulation according to the present invention assessed over a period of seven days, demonstrating the stability of formulations.
Figure 4:
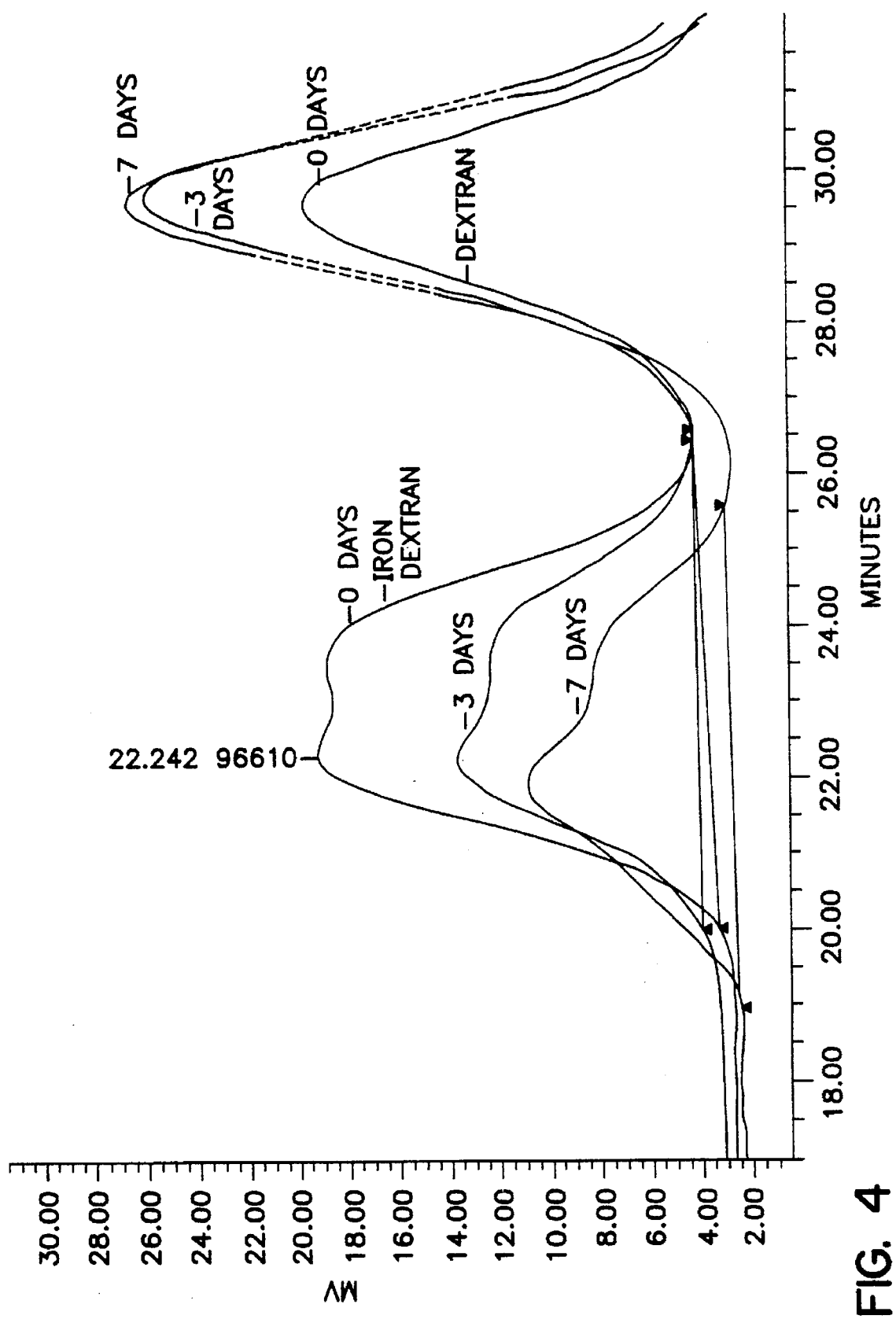
FIG. 4 shows the HPGPC chromatogram of a commercial iron dextran formulation assessed over a period of seven days, demonstrating a significant instability relative to the formulation of FIG. 3. At a magnification of 140,000 times.

The present inventors have found that iron dextran formulations prepared according to the following specifications are surprisingly more temperature stable and/or exhibit a much greater degree of homogeneity than is evidenced by or would have been expected from iron dextran formulations of the prior art such as IMFERON® and INFED®. The improved methods and compositions disclosed for the preparation of these iron dextran formulations achieve uniform molecular weight distribution. Safety, reliability and quality of iron dextran injectable and infusible products can be significantly improved over previous products. Our product now in development is called DEXFERRUM®. DEXFERRUM® is a pharmaceutically-equivalent iron dextran characterized by a higher mean molecular weight (266,608±1.4% daltons).

In the following discussion and examples, certain calculations as set forth below are required to determine the amounts of active and inactive ingredients:

The amount of iron dextran is based on its iron ($Fe^{3+}$) content. The amount in mg/ml is calculated by dividing the desired iron concentration in mg/ml of elemental iron by the powder's % w/w iron content divided by 100. This amount is then multiplied by the batch size in liters for the amount required in grams for that batch size. This value is then corrected for its moisture content.

In general, a suitable iron III salt, such as ferric chloride, is neutralized with a suitable alkali to which a modified dextran is added either before, concomitantly or after neutralization to produce an iron dextran complex with a molecular weight in the range of about 100,000 to about 600,000 daltons. The resulting solution is purified of excess dextran, salts, toxic impurities, etc., such as are identified in Table 2 by any suitable method to produce an iron dextran aqueous concentrate or powder with an elemental iron concentration of between about 5% to about 50%. Purified iron dextran powder or concentrate is then used in the preparation of a final solution made of the foregoing iron dextran composition, with an elemental iron content of about 25 to about 100 mg/ml.

We have observed that in solution, dextran is not tightly bound to the iron core, and complexes formed of aggregates in which, e.g., two cores might be bound to the same dextran molecule, can be observed. The dextran serves to stabilize the core, but the purification process associated with the initial preparation of iron dextran particles in which, e.g., chloride iron is removed, also tends to remove some of the dextran.

To a final solution made of the foregoing iron-dextran composition, an appropriate amount of oxidized dextran is added to provide a desired final ratio of the content of iron to dextran in the final iron dextran composition in a range from about 1:2 to 1:5, but preferably about 1:4 as described in greater detail below. The iron-dextran and oxidized dextran mixture is heated and reacted for an appropriate length of time with a suitable alkali. Generally, an appropriate length of time is not less than about one hour. The actual amount of time required to complete the reaction is dependent on the amounts and ratios of starting materials. Determination of the end point may be measured by the absence of dextran enhancement of the LAL endotoxins test. We have determined that oxidized dextran enhances the LAL gel clot method for assessing endotoxins, whereas reacted material, prepared according to our disclosure, demonstrates no such enhancement. Thus, in our manufacturing procedure, the reaction end point is determined by this technique to be complete when the amount of unreacted dextran does not exceed about 0.05 percent. After cooling and dilution to a final volume, the pH of the solution is adjusted to a physiologically acceptable pH range. This adjusted solution is then aseptically filled and/or terminally sterilized for administration, such as by injection.

We believe that the reaction of the iron dextran complex with an oxidized dextran under alkaline conditions converts the terminal unit of oxidized dextran from δ-Gluconolactone to sodium gluconate. The resulting solution contains dextran that is both bound and unbound to the iron complex where the molecular weight distributions of the bound and unbound dextrans are in equilibrium. Without wishing to be bound by any particular mechanism of action, we believe that the oxidized dextran at this stage of processing of iron dextran compositions minimizes or substantially eliminates aggregate complexes in which two iron cores might be bound to the same dextran molecule. Moreover, oxidized dextran has a terminal carboxyl group and has superior chelating abilities.

The amount of oxidized dextran required to produce the desired product meeting its desired nonvolatile residue is calculated by subtracting the calculated # mg/ml iron dextran (dry weight) from the theoretical total weight based on the nonvolatile residue of the desired product. That is, for a nonvolatile residue of 28–43 % w/v, the theoretical total weight would range from 280 to 430 mg/ml. The value obtained is then corrected for the oxidized dextran's loss on drying by dividing this value by (1-(loss on drying/100)). This amount is then multiplied by the batch volume in liters for the amount of grams for that batch size.

The amount of alkali (such as sodium hydroxide) is dependent on the amount of oxidized dextran since it reacts with the alkali to form a carboxylic acid. The reaction is 1:1. To determine the appropriate amount of alkali (such as NaOH) in grams, the molecular weight of the alkali is multiplied by the number of grams of oxidized dextran required for the desired product which is then divided by the average molecular weight of the oxidized dextran.

A maximum limit for the hydrochloric acid used to adjust pH is calculated using the desired product's upper limit for chloride content. The amount of chloride supplied by the starting materials (iron dextran and oxidized dextran) is calculated, then the maximum amount of hydrochloric acid added is determined by subtracting the total amount of chloride supplied from the starting materials from the desired product's upper limit for chloride content, then multiplying the value obtained by the batch size in liters, divide this value by the atomic weight of chloride (35.5) and then divide by the normality of the hydrochloric acid solution to be used for the final value.

The low molecular weight carbohydrates of the invention must be oxidized in order to avoid problems in lack of uniformity and with the presence of endotoxins. Such carbohydrates preferably have a molecular weight in the range of about 2,000 to 15,000 daltons, most preferably around 6,000 to 7,000 daltons. The preferred concentrations of the carbohydrates of the invention which effectively impart stabilization to the carrier phase of the metal oxide composition are in the range of about 0.001M to about 2M, most preferably about 0.05M to about 0.5M, but optimal concentrations can be determined by those skilled in the art according to conventional techniques.

Some preferred low molecular weight stabilizing agents include, but are not limited to, mannitol, sorbitol, glycerol, inositol, dextran 1 (Pharmacia Inc., Piscataway, N.J.) and ascorbate. Other useful agents include dextrins, celluloses, hydroxyethylstarches, heparins, starches, dextran sulfates, carboxylmethylated dextran and carboxymethyl cellulose. In the case of dextran 1, which has a molecular weight of about 1,000 daltons, the same compound can both stabilize the colloid or particulate suspension against unwanted physical changes and block possible adverse reactions. The simultaneous injection of dextran 1 and a complex of dextran and the magnetic iron oxide decreases adverse reactions to high molecular weight dextran alone.

Preferred methods of manufacture of iron dextran solutions involve the neutralization of ferric chloride solution with an alkaline solution of dextran. The mixture is heated, then cooled to room temperature and clarified by centrifugation. The resulting solution is then concentrated to the desired iron content by dialysis against running water. The iron dextran is composed of a beta-FeO(OH) core formed by the neutralization of an acidic ferric chloride/dextran solution with alkaline sodium bicarbonate. The by-products of this reaction are sodium chloride and carbon dioxide. During neutralization, the modified dextran is absorbed (complexes) to the iron core's surface where the dextran's hydroxyl groups provide the "OH" needed for stabilization of the core's beta-FeO(OH) structure.

EXAMPLES

Experimental studies describing the use of low molecular weight carbohydrates as stabilizing agents for metal oxide compositions prepared according to the present invention are presented below. These examples are to be considered as illustrative of the present invention rather than limitative of its scope in any way.

The preferred dextran formulation for the production of iron dextran formulations according to the present invention are prepared by fermentation of sucrose using *Leuconostoc mesenteroides* bacteria (NRRL B-512 (F)). The crude dextran is precipitated, hydrolyzed, and fractionated by conventional means. The dextran fraction is oxidized with an oxidizing agent under alkaline conditions, then purified.

Studies on the structure of the iron dextran complex report that it is composed of a beta-FeO(OH) core complexed with low molecular weight dextrans ranging from 3,500 to 7,500 daltons. The oxidized dextran used in this invention is the dextran which is depolymerized to an average molecular weight ranging from 3,500 to 7,500 daltons. The dextran's terminal unit, D-glucose, is then oxidized to gluconolactone. During the manufacturing process described in this invention the oxidized dextran's terminal unit, gluconolactone, is converted to D-glucuronic acid via alkaline hydrolysis.

The oxidized dextran used to produce iron dextran products according to the present invention has the following physical properties as set forth in Table 1:

TABLE 1

| Parameter | Tolerance |
| --- | --- |
| Description | White, amorphous powder |
| odor | Odorless |
| Loss on Drying (w/w %) | Not more than 5.0% |
| Sodium chloride content (w/w %) | Not more than 2.0% |
| Nitrogenous Impurities | Not more than 0.015% |
| Bromide content | Less than 5 ppm |
| Alcohol and Related Impurities | Less than 0.05% w/w |
| Relative Viscosity of a 10 % sol | Less than 4.0 centistokes |
| Average Molecular Weight | Between 3,000 and 7,000 |
| Phosphate (w/w %) | Not more than 0.28% |
| Reducing Sugars (w/w %) | Not more than 7.0% |
| Pyrogen Test | Passes test |

The characteristics and physical properties of the preferred iron dextran powder used to produce iron dextran formulations of the present invention are as follows in Table 2. This composition is commercially available from Laboratorien Hausmann AG in Switzerland, and U.S. Pat. No. 4,599,405, discussed above, is relevant to the preparation of such compositions. U.S. Pat. No. 3,697,502 also is relevant.

TABLE 2

| Parameter | Tolerance |
| --- | --- |
| Description | Brown, amorphous powder |
| Identification | Complies |
| Loss on Drying (w/w %) | Not more than 10.0% |
| Sodium chloride content (w/w %) | Not more than 6.0% |
| Dextran content | Between 29.0 and 36.0% |
| Iron Content | Between 28.0 and 35.0% |
| Bromide content | Less than 5 ppm |
| Alcohol and Related Impurities | Less than 0.05% w/w |
| pH of a 5% Solution | 5.2 to 6.5 |
| Molecular Weight Determination by GPC | |
| $M_w$ | Between 255,000–520,000 |
| $M_n$ | Between 200,000–365,000 |

TABLE 2-continued

| Parameter | Tolerance |
| --- | --- |
| $M_w/M_n$ | Not more than 1.7 |
| Arsenic | Not more than 2 ppm |
| Lead | Not more than 100 ppm |
| Copper | Not more than 100 ppm |
| Zinc | Not more than 100 ppm |
| Bacterial Endotoxins | Passes test |

EXAMPLE 1

Preparation of Iron dextran Compositions

In a 200 liter steam-jacket reaction vessel, 114 liter of hot (70° C. –90° C.) water was added. Next, 30.0 kg of iron dextran, satisfying the parameters described above, along with 28.3 kg oxidized dextran, also satisfying the parameters discussed above. The mixture was diluted up to 175 liters. Next, 185 g of NaOH was added and mixed with the iron dextran mixture. The vessel was sealed and then heated to a range of 110° C.–115° C. using a steam jacket for three hours. The vessel was then cooled to approximately 25° C. and vented during the cooling process. The pH was tested and adjusted to the range of 5.7–6.0.

The reaction solution was prefiltered through a 1.0 micron membrane into a holding vessel. Next, the filtered solution was passed through a 0.2 micron filter into sterilized receiving vessels, and depyrogenated vials were filled and stoppered with aliquots of the sterilized solution.

EXAMPLE 2

Evaluation of Process Results to Determine Molecular Weight Using HP-GPC

The molecular weight of the iron dextran complex of Example 1 was determined by gel permeation chromatography in a HP-GPC system equipped with a differential refractometer as the detector and an integrator with a GPC program for molecular weight calculations. The HP-GPC column was packed with porous particles of polyacrylic acid containing pore sizes up to 1000 angstroms. The pores act as sieves where smaller molecules permeate through in the packing's pores while the larger molecules are excluded from the packing and are eluted by the more mobile phase. Thus, macromolecules elute from the columns, from largest to smallest.

FIGS. 1–4 show comparisons between the iron dextran formulations of the present invention and two commercial preparations. These figures present data generated by a refractive index detector. This detector measures the concentration of the iron dextran, dextran and other molecules and the integrator's GPC program interprets the data and calculates the relative: weight average molecular weight (Mw), number average molecular weight (Mn) and polydispersity index (Mw/Mn) of the sample. The reported values are based on polyethyleneglycol (PEG) and polyethylenoxide (PEO) standards used for calibration of the instrument, and are considered relative molecular weights which should be within 5% of the actual values.

Figure 5:
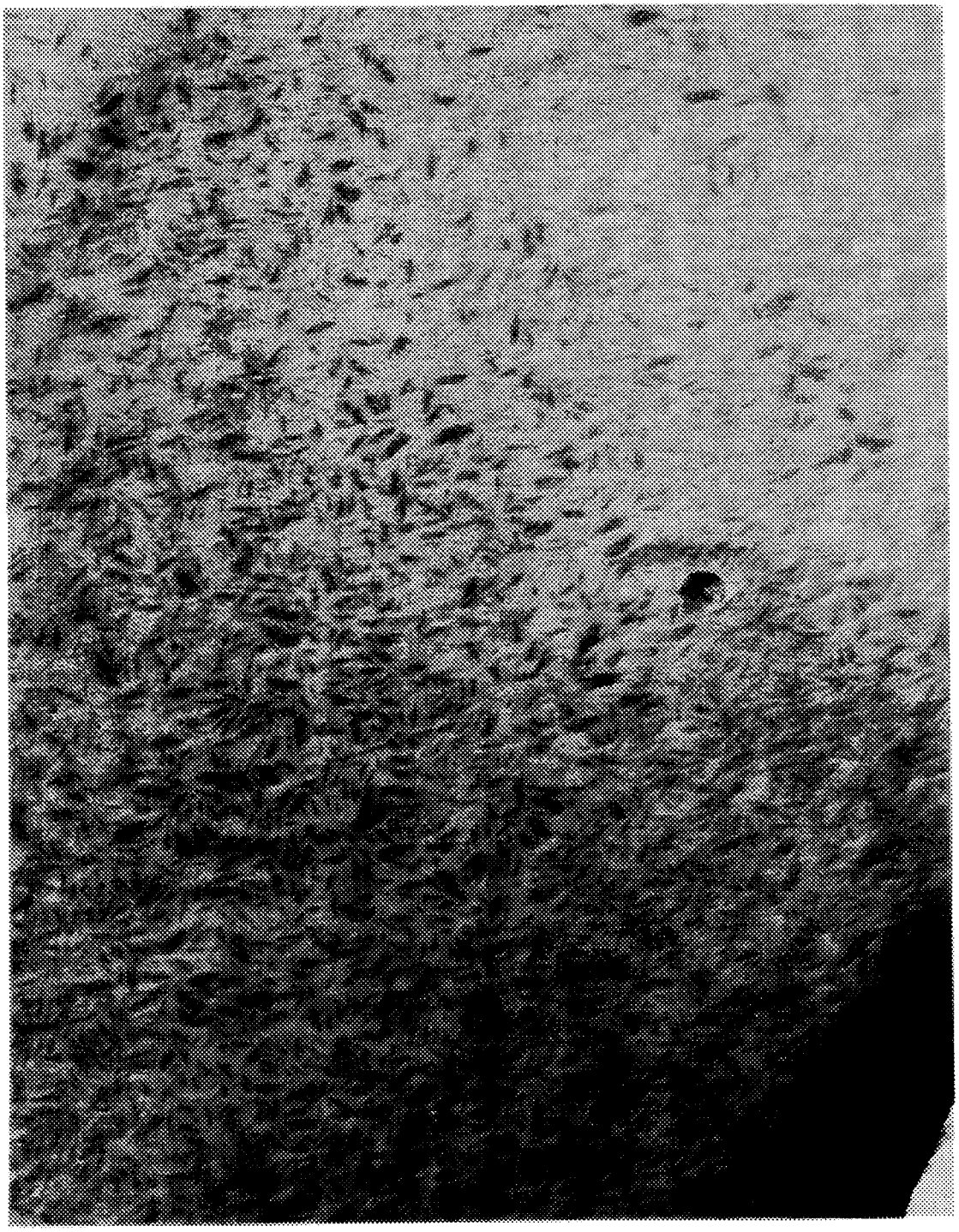
FIG. 5 shows that an electron photomicrograph of iron dextran particles according to the present invention at a magnification of 140,000×.
Figure 6:
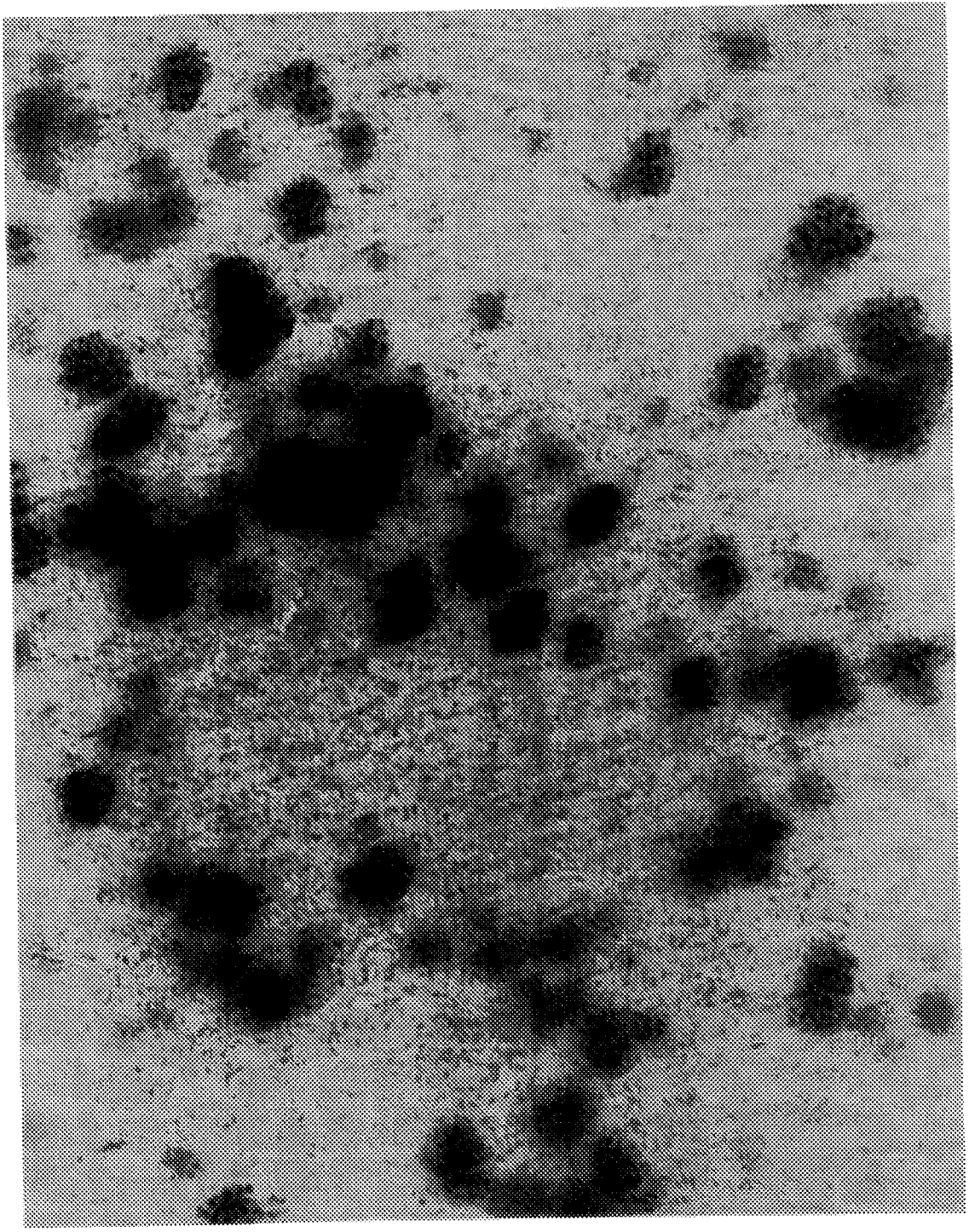
FIG. 6 shows electron photomicrograph of particles sold under the brand name INFeD® at a magnification of 140,000×.

Ellipsoidal particles of the present invention are shown in FIG. 5. This shows DEXFERRUM® at a magnification of about 140,000×. In comparison, FIG. 6 shows particles sold under the name INFeD®. The unique conformation and consistency of the DEXFERRUM® particles, as compared with another iron dextran supplement product, is evident from the foregoing figures and comparative electron photomicrographs. This information is consistent with the literature analyses of prior art iron-dextran complexes as reflected in the paper by Cog, et al, from *J. Pharm. Pharmac* 24:513–517 (1972).

The DEXFERRUM® particles typically range in length from about 31.5 to about 36.5 nanometers and are approximately 4.5 nanometers in width. The IMFERRON® particles by photomicrograph have a core also in an ellipsoid shape but ranging in size from about 13.5 to 18 nanometers in length with a width ranging from about 9 to about 13.5 nanometers. These electron photomicrographs are not shown. FIG. 6, which shows the INFeD®product, reveals iron cores also in the form of thin ellipsoids with a length of about 13.5 to 18 nanometers with an average width of about 4.5 nanometers. As FIG. 5 indicates, the DEXFERRUM® particle is substantially uniform in terms of particle size and shape. FIG. 6 shows a relative heterogeneity of the comparable INFeD® product.

EXAMPLE 3

Human Plasma Residence Time

The following Table 3 demonstrates that the plasma residence time of the new iron dextran prepared according to the present invention is significantly longer than that of other commercial iron dextran formulations.

TABLE 3

| Plasma Residence Time of Iron Dextrans* | |
|---|---|
| Products | Half life (hours) |
| IMFERON | 5.9 |
| INFED | 34.2 |
| DEXFERRUM | 58.9 |

*The plasma half-life figures assume a standard intravenous dose of 100 mg of elemental iron. IMFERON® determination used a radio-isotope label of iron $^{59}$Fe, while INFeD® and DEXFERRUM® had direct measurement of iron dextran in plasma.

EXAMPLE 4

Comparison of Indicators of Iron Dextran Efficacy

Measurements of transferrin, plasma ferritin and hemoglobin levels are the major indicators of iron dextran efficacy. The following Tables 4 and 5 demonstrate that the iron dextran according to the present invention are biologically comparable to an existing commercial preparation. Levels of hemoglobin, serum ferritin, serum iron and total iron binding capacity (the serum iron divided by the total iron binding capacity times 100%) were determined by standard CLIA monitored commercial clinical laboratory assays.

TABLE 4

| Comparison of Transferrin Levels Transferrin AUC 0–96 hours (ug*hr/dL) | |
|---|---|
| Iron Dextran Invention | Commercial #2 |
| 11,510 | 11,316 |

TABLE 5

| Comparison of Hemoglobin and Ferritin Levels | | | | |
|---|---|---|---|---|
| Days | Hemoglobin Comm. #2 | Hemoglobin New Iron Dextran | Ferritin Comm. #2 | Ferritin New Iron Dextran |
| 0 | 10.7 | 10.3 | 122.8 | 104.1 |
| 7 | 10.9 | 11.1 | 255.5 | 619.8 |
| 14 | 11.3 | 11.2 | 205.8 | 233.8 |
| 21 | 11.0 | 11.4 | 186.8 | 213.3 |
| 28 | 11.0 | 11.4 | 194.5 | 193.2 |

EXAMPLE 5

Comparison of Biological Equivalence Between INFeD® and DEXFERRUM®

To examine the pharmacokinetics of iron dextran in hemodialysis patients, we serially determined iron dextran concentrations in the serum of 20 patients after 100 mg IV (intravenous) iron dextran was administered. By this study, we determined whether treatment with DEXFERRUM® versus INFeD® was biologically equivalent for the pharmacokinetic parameters, since DEXFERRUM® is an iron dextran preparation, according to the process of the present invention. DEXFERRUM® has a higher average molecular weight than INFed®, i.e., about 300,000 daltons to 180,000 daltons. The clinical design was a 2-period crossover study with patients randomized to receive either DEXFERRUM® followed by INFed® or INFeD® followed by DEXFERRUM®. Blood samples were obtained at specified times after the end of drug infusion.

A comparison of the results for area-under-the-curve suggested a statistically significant difference between the two treatments, with no statistically significant difference in the observed maximum blood concentration. Analysis of secondary parameters, suggested a statistically significant difference in the half-lives, but no difference in the volumes observed for the two treatments.

Iron deficiency in dialysis-associated anemia is heralded by a falling hematocrit, or increasing Epoetin alfa requirements to maintain target hematocrit, coupled with a declining serum transferrin saturation and serum ferritin. See, e.g., Van Wyck DB, *Iron Balance in Dialysis Patients*, Healthmark, N.Y. (1989); Eschbach, J. W. et al., Ann. Intern. Med. 11:992 (1989); McEvory, G. K. ed. *AHES: Drug Information '92*, American Society of Hospital Pharmacists, pages 766–768 (1992); and Gimenez, L. F. et al., Hematology/Oncology Clinics 8:913 (1995).

Unfortunately, oral iron supplements do not reliably restore iron balance, probably because intestinal absorption of low doses is limited, high doses promote GI toxicity and noncompliance, and any benefit to body iron balance is outstripped by iron deficits due to dialysis-associated or pathologic blood loss. When oral supplementation fails to prevent iron deficiency in dialysis-associated anemia, therapy with intravenous iron dextran is indicated. See, Eschbach, J. W. et al., cited above; and Van Wyck, D. B., et al., Kid. Int. 35:712 (1989).

The effective bioavailability of iron dextran given intravenously depends on clearance of the iron dextran colloid from the plasma space. Previous information in patients with normal renal function has shown that radiolabelled iron dextran after IV administration is removed from the plasma by the reticuloendothelial system. See, Eschbach, J. W. et al., and Henderson, et al., cited above. Though iron deficiency in patients with dialysis-associated anemia is a frequent indication for iron dextran therapy, information on pharmacokinetics of iron dextran in patients with renal failure is lacking. Nor are data available describing pharmacokinetics of an unlabelled product.

The physiologic response to anemia in individuals with normal renal function is characterized by increased production of erythropoietin by the kidney. In chronic renal failure, erythropoietin production fails, and progressive anemia routinely ensues. Prior to the introduction of recombinant human erythropoietin (in North America, Epoetin alfa; produced by Amgen and OrthoBiotech), virtually all chronic hemodialysis patients suffered dialysis-associated anemia, and 25% required frequent transfusions to maintain the hematocrit in a life-sustaining range.

The use of Epoetin alfa successfully reverses transfusion dependency and raises hemoglobin and hematocrit into a range compatible with health. Nevertheless, the therapeutic efficacy of *Epoetin alfa* is frequently thwarted in practice by the development of iron deficiency. Iron deficiency in dialysis-associated anemia is heralded by a falling hematocrit, or an increasing *Epoetin alfa* requirement to maintain target hematocrit, coupled with a declining serum transferrin saturation and serum ferritin.

Several other factors also contribute to the ongoing negative iron balance experienced by hemodialysis patients. First and foremost, the dialysis procedure itself is associated with blood loss, from the needle stick and from retention of red cells within the dialyzer microtubules. Though the volume lost with each dialysis is small, the cumulative loss of iron is estimated to amount to greater than 1 gram annually. Since the diet of the dialysis patient is restricted by prescription in the foods richest in iron (red meat), little iron is available to dialysis patients from nutritional sources.

Oral iron is commonly prescribed. However, despite the observation that intestinal iron absorption in chronic renal failure is intact, meals, antacids, a multiplicity of medications, and a high incidence of gastritis and constipation conspire against the effectiveness of oral iron supplements. Iron deficiency marked initially by a fall in ferritin level, followed by a drop in the transferrin saturation, and eventually, as iron deficiency erythropoiesis slows red cell production, by iron deficiency anemia or an increasing demand for *Epoetin alfa*. When oral supplementation fails to prevent iron deficiency in dialysis-associated anemia, therapy with intravenous iron dextran is indicated.

Evidence in patients with iron deficiency anemia and normal renal function suggests that recovery of iron for hemoglobin synthesis or iron stores early after intravenous iron dextran infusion is incomplete. Our previous retrospective analysis in patients with dialysis-associated anemia confirmed that quantitative iron utilization for hemoglobin or ferritin-related stores is highly variable and incomplete within the first 90 days after iron dextran infusion.

To forestall declining hematocrit or increasing *Epoetin alfa* doses, iron dextran is administered early in iron deficiency, whenever the ferritin falls below 100 ug/L or the transferrin saturation falls below 20%. Our data confirm that, when iron dextran is given in this early stage of iron deficiency, when storage iron depletion is present but worsening anemia or *Epoetin alfa* resistance has not yet occurred, therapeutic efficacy is marked by a rise in serum ferritin, signifying repletion of iron stores, without a concomitant increase in hemoglobin.

In the current study, we examined iron utilization after infusion of five 100 mg infusions of iron dextran, INFeD®, in iron deficient patients receiving *Epoetin alfa* for dialysis-associated anemia. We compared results with those seen in patients after an equimolar dose of iron dextran, DEXFERRUM®. The 500 mg is a standard therapeutic dose for iron deficiency in iron anemic dialysis patients.

This was an active treatment control study using a randomized, unblinded design. The purpose of the study was to determine whether treatment with DEXFERRUM®, when compared with INFeD®, is biologically equivalent for hemoglobin synthesis and ferritin-related stores in patients undergoing hemodialysis for end-stage renal disease who meet the requirements for parenteral iron supplementation. The primary study outcome was the percent mobilization of iron from iron dextran. Results after iron dextran INFeD® (Schein Pharmaceuticals, Phoenix, Az.) were compared to those after equimolar administration of DEXFERRUM® (Luitpold Pharmaceuticals, Shirley, N.Y.).

Secondary study outcomes included serum ferritin, total body iron, hemoglobin, serum iron, total iron binding capacity (TIBC), and serum transferrin saturation. We also examined adverse events after administration of each test dose and each therapeutic dose of iron dextran, and compared results after DEXFERRUM® to those after INFeD®. Five (5) single 100 mg IV doses (total dose: 500 mg) of each drug were administered to the patients in each group during five sequential dialysis sessions (see FIG. 1 in section titled "Study Design").

EXAMPLE 6

Iron Mobilization Early After Iron Dextran Infusion in Hemodialysis Patients

To determine the reliability of serum iron indices and the degree of iron utilization early after iron dextran infusion, we measured iron status before and at weekly intervals after a total course of 500 mg IV iron dextran INFeD® in 11 iron-deficient patients receiving chronic hemodialysis and *Epoetin alfa* for dialysis associated anemia. Oral iron therapy was withheld and evidence of bleeding, infection, inflammation, recent surgery or transfusions was absent. Mobilization was calculated by expressing the increase in body iron as a percent of total iron administered (Van Wyck, et al. cited above):

Iron stores=400×[log(ferritin)–log(3)]

Red cell iron=150×(Hbg)

% Mobilization=$\{[(A_0-A_1)! (B_0-B_1)]/500\}=100\%$ where $A_0$ and $B_0$ are values for stores and red cell iron, respectively, at time zero, and $A_1$ and $B_1$ are values at intervals afterwards. Results±SD) are as follows in Table 6:

TABLE 6

| Day | Hgb | % Saturation | Ferritin | % Mobilization |
|---|---|---|---|---|
| 0 | 10.8 ± 0.9 | 17.2 ± 7.4 | 104.7 ± 84 | — |
| 7 | 11.1 ± 1.1 | 22.1 ± 9.5 | 215.6 ± 107 | 38.6 ± 26 |
| 14 | 11.6 ± 1.0 | 19.9 ± 7.6 | 198.6 ± 108 | 50.8 ± 29 |

TABLE 6-continued

| Day | Hgb | % Saturation | Ferritin | % Mobilization |
|---|---|---|---|---|
| 21 | 11.2 ± 1.0 | 20.1 ± 7.1 | 176.7 ± 102 | 32.7 ± 28 |
| 29 | 11.3 ± 0.9 | 18.9 ± 6.9 | 182.9 ± 117 | 37.8 ± 25 |

The increase in hemoglobin and ferritin was statistically significant (<0.02). Thus, in the presence of *Epoetin alfa* therapy, 1) ferritin and hemoglobin rise quickly after IV iron dextran, and 2) an early rise in transferrin saturation is transient, due to early incorporation of iron into hemoglobin and iron stores, 3) which is, in the first four weeks, highly variable and predictably incomplete. Accordingly, decisions to repeat iron dextran therapy based on low transferrin saturation should be weighed against the observation that, within the first month after IV administration, most of the original iron dose remains physiologically unavailable.

Based on the foregoing discussion and experimental data, one skilled in the art would readily be able to modify the production processes in order to optimize reaction and administration conditions for particular compositions of iron dextran. Thus, the following claims should be considered as defining our invention, rather than the foregoing specific examples. All articles and patent references are hereby incorporated by reference in their entireties.

What we claim is:

1. An iron-dextran composition for treating iron deficiency comprising an aqueous colloidal suspension or solution of a ferric oxyhydroxide-dextran complex in a physiologically acceptable carrier, said complex having a beta-FeO(OH) core and an average molecular weight range of about 100,000 to 600,000 daltons and a substantially uniform size distribution, said complex further having been treated under alkaline conditions with an oxidized low molecular weight carbohydrate stabilizing agent and having an increased plasma residence time as compared with iron-dextran compositions that have not been so treated.

2. The composition of claim 1, wherein said stabilizing agent is selected from the group consisting of mannitol, sorbitol, glycerol, inositol, ascorbate, dextrin, cellulose, carboxymethyl cellulose, starch, hydroxyethylstarch, heparin, dextran, dextran sulfate and carboxylmethylated dextran.

3. The composition of claim 1, wherein said average molecular weight is about 150,000 to 350,000 daltons.

4. The composition of claim 1, wherein said average molecular weight is about 250,000 to 300,000 daltons.

5. The composition of claim 1, wherein said complex has the shape of an ellipsoid.

6. The composition of claim 5, wherein said ellipsoid has an average length of about 25 to 45 nanometers and a width of about 3.5 to 5.5 nanometers.

7. The composition of claim 6, wherein said ellipsoid has an average length of about 31.5 to 36.5 nanometers and a width of about 4 to 5 nanometers.

8. The composition of claim 1, wherein the iron component of said complex comprises an initial iron dextran preparation having particles with a molecular weight ranging from about 100,000 to 600,000 daltons and the low molecular weight stabilizing agent component of said complex comprises an oxidized dextran of low molecular weight ranging from about 1,000 to 15,000 daltons.

9. The composition of claim 8, wherein said oxidized dextran has a molecular weight of about 6,000 daltons.

10. The composition of claim 8, wherein the pH is adjusted to about 5.2 to 6.5.

11. The composition of claim 2, wherein said stabilizing agent is dextran.

12. The composition of claim 1, wherein said core is formed during the neutralization of an acidic ferric chloride/dextran solution with an alkali.

13. A method for making an iron dextran composition for treating iron deficiency, comprising the steps of:

preparing an iron dextran suspension, said suspension comprised of iron dextran particles having a beta-FeO(OH) core;

purifying said composition by the removal of contaminants and by-products inconsistent with administration to mammalian patients;

reacting said iron dextran complex under alkaline conditions with an oxidized low molecular weight carbohydrate stabilizing agent; and purifying the iron dextran composition in the form of iron-dextran complexes, said complexes having an increased plasma residence time as compared with iron-dextran compositions that have not been so treated.

14. A method for reducing anemia in a human or animal subject comprising the administration of a pharmaceutically acceptable dose of the composition of claim 1.

15. A method for reducing anemia in a human or animal subject comprising the administration of a pharmaceutically acceptable dose of the composition of claim 11.

16. A stable injectable iron dextran solution prepared by the method of claim 13.

17. The composition of claim 13, wherein said stabilizing agent is selected from the group consisting of mannitol, sorbitol, glycerol, inositol, ascorbate, dextrin, cellulose, carboxymethyl cellulose, starch, hydroxyethylstarch, heparin, dextran, dextran sulfate and carboxylmethylated dextran.

18. The method of claim 17, wherein said stabilizing agent is dextran.

19. The method of claim 15, wherein said dextran has an average molecular weight in the range from about 1,000 to 15,000 daltons.

20. The method of claim 16, wherein said dextran has an average molecular weight of about 6,000 daltons.

21. The method of claim 13, wherein the pH of the composition is adjusted to about 5.2 to 6.5.

22. The method of claim 13, wherein said complexes have an average molecular weight in the range from about 150,000 to 350,000 daltons.

23. The method of claim 22 wherein said average molecular weight is about 250,000 to 300,000 daltons.

24. The method of claim 17, wherein said complexes have the shape of an ellipsoid.

25. The method of claim 24, wherein said ellipsoid has an average length of about 25 to 45 nanometers and a width of about 3.5 to 5.5 nanometers.

26. The method of claim 25, wherein said ellipsoid has an average length of about 31.5 to 36.5 nanometers and a width of about 4 to 5 nanometers.

27. An iron-dextran composition produced by the process of claim 13.

28. The composition of claim 27, wherein said composition is formulated for parenteral human administration in a physiologically acceptable carrier.

* * * * *